(12) United States Patent
Rasooly et al.

(10) Patent No.: US 10,577,667 B2
(45) Date of Patent: Mar. 3, 2020

(54) SYSTEMS AND METHODS FOR MICROBIAL TOXIN DETECTION

(71) Applicant: The United States of America, as represented by the Secretary of Agriculture, Washington, DC (US)

(72) Inventors: Rueven Rasooly, El Sobrante, CA (US); Bradley J. Hernlem, Concord, CA (US); Paula M. Do, Richmond, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 15/646,177

(22) Filed: Jul. 11, 2017

(65) Prior Publication Data
US 2019/0017126 A1 Jan. 17, 2019

(51) Int. Cl.
| | |
|---|---|
| *C12Q 1/6897* | (2018.01) |
| *G01N 21/76* | (2006.01) |
| *C12Q 1/14* | (2006.01) |
| *G01N 21/64* | (2006.01) |

(52) U.S. Cl.
CPC .............. *C12Q 1/6897* (2013.01); *C12Q 1/14* (2013.01); *G01N 21/76* (2013.01); *G01N 21/6428* (2013.01); *G01N 21/763* (2013.01); *G01N 2333/31* (2013.01)

(58) Field of Classification Search
None
See application file for complete search history.

(56) References Cited

PUBLICATIONS

Viles et al., "Measurement of Marine Picoplankton Cell Size by Using a Cooled, Charge-Coupled Device Camera with Image-Analyzed Fluorescence Microscopy" 58(2) Applied and Environmental Microbiology 584-592 (1992).*
Contag et al., "Advances in In Vivo Bioluminescence Imaging of Gene Expression" 4 Annual Review of Biomedical Engineering 235-260 (2002).*
Rasooly et al., "Sensitive, Rapid, Quantitative and in Vitro Method for the Detection of Biologicall Active Staphylococcal Enterotoxin Type E" 8 Toxins 150, 1-11 (May 13, 2016).*
Rasooly et al., "TNF as Biomarker for Rapid Quantification of Active *Staphylococcus* Enterotoxin A in Food" 12 Sensors 5978-5985 (2012) (Rasooly II).*
Yang et al., "Gold nanoparticle-based enhanced chemiluminescence immunosensor for detection of Staphylococcal Enterotoxin B (SEB) in food" 133 International Journal of Food Microbiology 265-271 (2009).*

* cited by examiner

*Primary Examiner* — Nancy J Leith
(74) *Attorney, Agent, or Firm* — John D. Fado; Robert Jones

(57) ABSTRACT

Systems and methods for detecting microbial toxins are disclosed. The system includes an imaging device operable to detect a luminescent signal and an analysis plate having a well to hold a sample containing the microbial toxin. The luminescence is created by a cell line expressing a product capable of reacting directly or indirectly with the microbial toxin to produce the luminescent signal. The signal is processed via an image processing system operable to receive the luminescent signal detected by the imaging device and convert the luminescent signal to a quantitative measurement correlated to an amount of the microbial toxin present in the sample.

19 Claims, 12 Drawing Sheets

Vero cells treated with CMV-Luc and AFB1,
measured with a plate reader or CCD Camera

FIG.11

Vero cells with CMV-Luc treated with Abrin toxin and measured with CCD camera

SYSTEMS AND METHODS FOR MICROBIAL TOXIN DETECTION

FIELD OF THE INVENTION

The disclosed invention relates generally to systems and methods to detect the presence of microbial toxins. More specifically, the invention relates to the utilization of cell-based assays to rapidly and economically quantify and differentiate low levels of active microbial toxins using image capturing technology to detect chemiluminescence activated by exposure to microbial toxins.

BACKGROUND OF THE INVENTION

Food-borne illness such as food poisoning is a major global threat to health. The Centers for Disease Control and Prevention (CDC) estimates that each year 1 in 6 Americans (about 48 million) people get sick from foodborne pathogenic microbes, about 128,000 are hospitalized, and about 3,000 die of foodborne diseases. In the U.S., about 240,000 illnesses, 1,000 hospitalizations, and 6 deaths per year are thought to be caused by staphylococcal food poisoning. The bacterium, Staphylococcus aureus synthesizes more than two dozen subtypes of staphylococcal enterotoxins (SE) that are responsible for foodborne illness and produces two related but separate biological responses: gastrointestinal targeted emesis and superantigen activation of the immune system. The social and economic impact of such illness is considerable in terms of loss of working days, lower productivity, hospital expenses, and economical losses in the food industry. The most common symptoms caused by ingestion of food contaminated with one or more subtypes of staphylococcal enterotoxins are nausea, violent vomiting, abdominal cramping, and diarrhea. The illness typically resolves within one to two days after onset, but in some cases can be severe enough to require hospitalization. Such toxins are a threat to both food safety and also food security if they are produced in a purified form that can be used as a deliberate adulterant.

One of the most common causes of food poisoning is the bacterium Staphylococcus aureus, which produces a wide range of exotoxins, including many subtypes of staphylococcal enterotoxins that have been associated with significant and frequent outbreaks in many parts of the world, in countries such as the United States, the United Kingdom, Japan, and France (see e.g., Bergdoll M. S., et al., 1971, Identification of enterotoxin E. Infect Immun 4(5):593-5; Wieneke A. A., et al., 1993, Staphylococcal food poisoning in the United Kingdom, 1969-90. Epidemiol Infect 110(3): 519-31; Asao T., et al., 2003, An extensive outbreak of staphylococcal food poisoning due to low-fat milk in Japan: estimation of enterotoxin A in the incriminated milk and powdered skim milk. Epidemiol Infect 130(1):33-40; Ostyn A., et al., 2010, First evidence of a food poisoning outbreak due to staphylococcal enterotoxin type E, France, 2009, Euro Surveill 15(13)). Examples of the many sources of potential staphylococcal enterotoxin contamination include manual contact, respiratory secretions, food animals, and dairy cattle. As a result, staphylococcal enterotoxins commonly contaminate meat, poultry, egg, and dairy products as well as vegetables, leafy greens, and baked goods, among others.

Current methods for the detection of active staphylococcal enterotoxin focus on the emetic effect of the toxin and involve the administration of a toxin laden sample to, for example, live monkeys, kittens, or guinea pigs either by gavage or intravenously (see e.g., Fulton, F., 1943, Staphylococcal enterotoxin—with special reference to the kitten test. Brit. J. Exp. Pathol. 24, 65; Bergdoll M. S., et al., 1971, Identification of enterotoxin E. Infect Immun 4(5):593-5; Bergdoll M. S., 1988, Monkey feeding test for staphylococcal enterotoxin. Methods Enzymol 165:324-33; Scheuber, P. H., et al., 1983, Direct skin test in highly sensitized guinea pigs for rapid and sensitive determination of Staphylococcal enterotoxin B. Appl. Environ. Microbiol. 46, 1351-1356). In addition to the ethical and regulatory concerns (e.g., Lautenberg Chemical Safety Act, which promotes the development and use of alternatives to animal testing for chemical toxicity methodologies), these animal model tests are also economically inefficient and have insufficient sensitivity for detecting low quantities of toxin. It has been reported that the animal-based method is not very sensitive and generally requires 5 to 20 mg of SE to cause 50% emesis in young monkeys (see e.g., Su, Y C & Wong, A C, Identification and Purification of a New Staphylococcal Enterotoxin, H., Appl Environ Microbiol, 1995, April 61(4), 1438-4343). In another report, it was shown that the response of monkeys to staphylococcal enterotoxins depends on the method of administration. For example, it was found that for intragastric administration the level of detection was 10 µg and for intravenous injection it was 0.5 µg (see e.g., Bergdoll M S, et al, Identification of enterotoxin E, Infect Immun, 1971, 4(5):593-5). Much lower limits of detection without the use of animal models are needed for industrial use and efficiency.

An alternative method to detect microbial toxins is chemically via, for example, enzyme-linked immunosorbent assay (ELISA) or by mass spectrometry (MS) (see e.g., Bennett R. W., 2005. Staphylococcal enterotoxin and its rapid identification in foods by enzyme-linked immunosorbent assay-based methodology. J Food Prot 68(6):1264-70; Dupuis A. et al., 2008, Protein Standard Absolute Quantification (PSAQ) for improved investigation of staphylococcal food poisoning outbreaks. Proteomics 8(22):4633-6). The lower limit of detection with such methods is generally about 0.25 to 1.0 ng/gr food (see e.g., Bennett R. W., 2005. Staphylococcal enterotoxin and its rapid identification in foods by enzyme-linked immunosorbent assay-based methodology. J Food Prot 68(6):1264-70). The main drawbacks of these chemical methods is the requirement of expensive instrumentation that is generally beyond the means of laboratories without many resources, and, in addition, the assays are unable to discern active toxin from inactivated toxin. Discerning between active and inactive toxin is important because food that has been treated or processed to reduce or eliminate toxin by inactivation may still test positive with these non-mechanistic (i.e., unable to discern between active and inactive toxin) assays.

There thus exists a challenging and urgent need for new systems and methods of detecting and identifying microbial toxins in a rapid, accurate, sensitive, and cost-effective fashion for governmental and non-governmental agencies, including the military, public health departments, healthcare facilities, and the food industry.

SUMMARY OF THE INVENTION

To address challenges and meet the regulatory, research, public health, and industrial needs, this invention accordingly provides systems and methods of quickly and efficiently detecting and quantifying microbial toxins. A novel and surprisingly sensitive in vitro approach is disclosed for detecting microbial toxins as well as differentiating between active and inactive microbial toxins. This invention provides economically favorable imaging technology to take advantage of chemiluminescence bioassays for detecting surprisingly low levels of microbial toxins.

In an aspect, the invention is a system for detecting a microbial toxin in a food matrix. The system includes an imaging device operable to detect a luminescent signal; a lens attached to the imaging device; optionally at least one secondary lens; an analysis plate having at least one well to hold a sample containing the microbial toxin; a cell line having a reporter gene expressing a product capable of reacting directly or indirectly with the microbial toxin to produce the luminescent signal; optionally an accessory cell line which when exposed to the microbial toxin displays the microbial toxin as an antigen on its surface to activate expression of the reporter gene expressing the product capable of reacting directly or indirectly with the microbial toxin to produce the luminescent signal; and an image processing system operable to receive the luminescent signal detected by the imaging device and convert the luminescent signal to a quantitative measurement correlated to an amount of the microbial toxin present in the sample.

In another aspect, the invention is a method of detecting a microbial toxin in a food matrix. The method includes (a) preparing the food matrix for analysis; (b) placing the food matrix in a sample well; (b) optionally exposing the food matrix to an accessory cell line which when exposed to the microbial toxin in the food matrix displays the microbial toxin as an antigen on its surface to activate expression of a reporter gene expressing a product capable of reacting directly or indirectly with the microbial toxin to produce a luminescent signal; (c) exposing the food matrix or the accessory cell line to a cell line having the reporter gene expressing the product capable of reacting directly or indirectly with the microbial toxin to produce the luminescent signal; (d) detecting the luminescent signal with an imaging device; (e) processing the luminescent signal with an image processor to create a processed luminescent signal; (f) converting the processed luminescent signal to a quantitative measurement correlated to an amount of the microbial toxin present in the food matrix.

In another aspect, the invention is a method of detecting a microbial toxin. The method includes (a) isolating the microbial toxin from a food matrix to create an isolated microbial toxin for analysis; (b) placing the isolated microbial toxin in a sample well; (c) optionally exposing the isolated microbial toxin to an accessory cell line which when exposed to the microbial toxin displays the microbial toxin as an antigen on its surface to activate expression of a reporter gene expressing a product capable of reacting directly or indirectly with the microbial toxin to produce a luminescent signal; (d) exposing the isolated microbial toxin or the accessory cell line to a cell line having the reporter gene expressing the product capable of reacting directly or indirectly with the microbial toxin to produce the luminescent signal; (e) detecting the luminescent signal with an imaging device; (f) processing the luminescent signal with an image processor to create a processed luminescent signal; and (g) converting the processed luminescent signal to a quantitative measurement correlated to an amount of the microbial toxin present in the food matrix.

It is an advantage of the invention to provide systems and methods for the rapid, economical, and sensitive detection of active bacterial enterotoxins involved in foodborne illnesses.

Another advantage of the present invention is to provide systems and methods of high throughput screening for bacterial toxins in industrial settings.

It is a further advantage of the present invention to provide systems and methods to efficiently test for the presence of active microbial toxins without false positives for inactive microbial toxins.

Yet another advantage of the present invention is to provide systems and methods of detecting microbial toxins using stable cell lines rather than live animals or cells harvested from sacrificed animals.

An additional advantage of the invention is to provide systems and methods of promoting food safety and security by making microbial toxin detection more efficient and widely available to industry as well as public health official to reduce outbreaks and trace the source of foodborne illness outbreaks.

A further advantage of the invention is to provide novel and vastly improved systems and methods for detection and quantitation of active microbial toxins.

This summary is provided to introduce a selection of concepts in a simplified form that are further described below in the detailed description. This summary is not intended to identify all key or essential features of the claimed subject matter, nor is it intended as an aid in determining the scope of the claimed subject matter.

BRIEF DESCRIPTION OF THE DRAWINGS

FIG. 11 shows an example of the ability of the disclosed system to detect the microbial toxin abrin from *Abrus precatorius*.

DETAILED DESCRIPTION OF THE INVENTION

Figure 1:
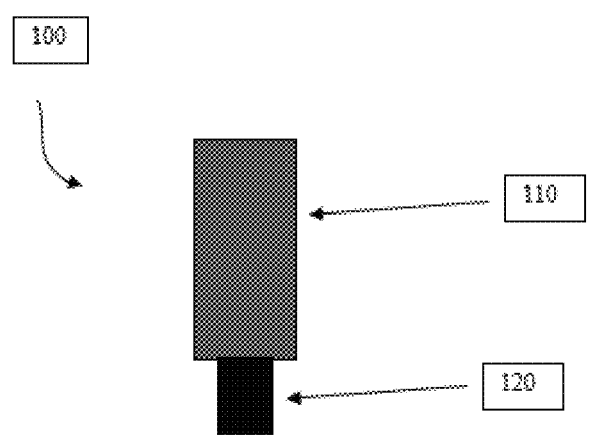
FIG. 1 shows an embodiment of a schematic configuration of a camera system and plate reader with the main system components highlighted in the schematic as imaging device 110, lens 120, analysis plate 130, well 140, and plate support 150.
Figure 1:
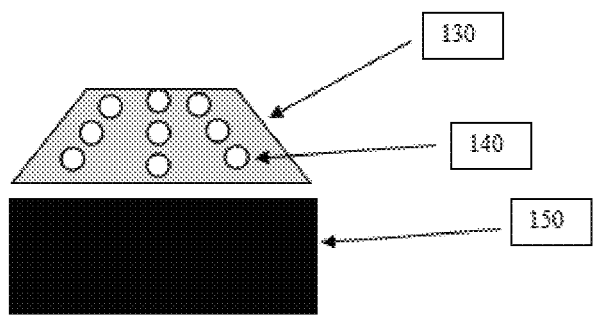
Figure 2:
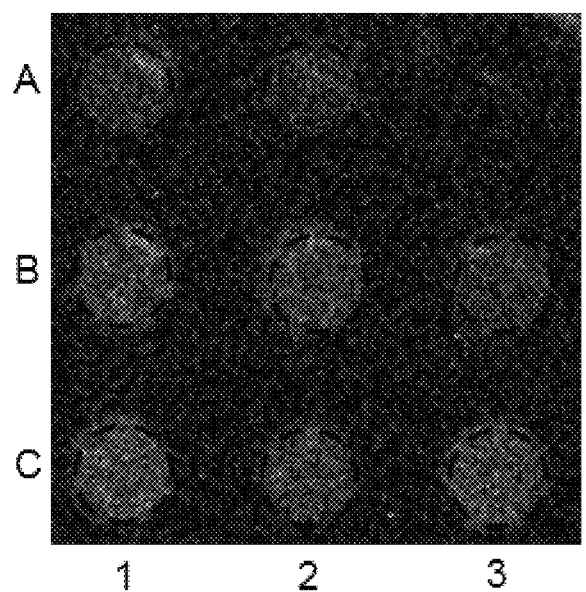
FIG. 2 shows an example image of a custom analysis plate and the dose-response relationship between microbial toxin concentration and luminescence light intensity emitted from the custom analysis plate.

Unless herein defined otherwise, all technical and scientific terms used herein generally have the same meaning as commonly understood by one of ordinary skill in the art to which this invention belongs. The definitions below may or may not be used in capitalized as well as singular or plural form herein and are intended to be used as a guide for one of ordinary skill in the art to make and use the invention and are not intended to limit the scope of the invention. Mention of tradenames or commercial products herein is solely for the purpose of providing specific information or examples and does not imply recommendation or endorsement of such products.

"Accessory Cell" means a cell line that is capable of displaying an antigen for presentation to a T-cell. For example, an accessory cell (sometimes referred to as an antigen-presenting cell or APC) may internalize an antigen via phagocytosis and display the antigen on its surface as a major histocompatibility complex (MEW) to a T-cell. The T-cell, in turn, recognizes the MEW which triggers a response from the T-cell.

"Camera" means any instrument capable of sensing and detecting and optionally recording, transmitting, and conveying, optical information that collectively creates an image.

"Cell Line" means any cell or strain engineered, transformed, and/or capable of expressing a reporter gene, including progeny and cultures thereof, to produce a chemiluminescent signal when the cell or strain is directly or indirectly exposed to one or more microbial toxins.

"Chemiluminescence" means luminescence (e.g., bioluminescence, fluorescence) or light emission resulting from any chemical or biological reaction.

"Enterotoxin" means members of a family of exotoxins produced and secreted by bacterial strains in the genii, for example, *Staphylococcus* and *Streptococcus*, such as *Staphylococcus aureus* and *Streptococcus pyogenes*. These exotoxins share a common phylogenetic relationship, structure, function, and sequence homology among at least 23 different currently known subtypes. Examples include staphylococcal enterotoxin (SE) subtypes A to E (i.e., SEA, SEB, SEC, SED, and SEE).

"Food Matrix" means the nutrient and non-nutrient components of foods, food products, food packaging, and their molecular relationships (i.e., chemical bonds) to each other including any class of solid, semi-solid, or liquid foods, juices, beverages, supplements, food packaging, the like, and any combinations thereof. Foods and food products include, for example fresh and processed (e.g., canned, jarred, juiced, preserved, frozen, dried, etc.) fruits and vegetables, fresh and processed (e.g., canned, jarred, preserved, frozen, dried, etc.) meats (e.g., beef, chicken, pork, fish, etc.), dairy products, nuts, parts or components thereof, the like, and any combinations of the foregoing.

"Luciferase" means any member of a class of oxidative enzymes found in several species (e.g., fireflies, sea pansies, copepods, plankton, microbes, and others) that catalyze a reaction which produces chemiluminescence under certain conditions. For example, fireflies emit chemiluminescent light via a luciferase-catalyzed enzymatic reaction in which luciferin is converted to oxyluciferin.

"Microbial Toxin" means any small molecule, peptide, or protein capable of causing illness or disease in humans or animals and produced by microorganisms, including bacteria and fungi.

"Regulatory Sequence" means any nucleotide sequence (e.g., transcription element, promotor, response element, enhancer element, the like, etc.) that is operably linked (directly or indirectly) to a reporter gene such and that it is capable of directing transcription of the reporter gene or synthesis of an enzyme or protein associated with the reporter gene.

"Reporter Gene" means a gene as part of an expression system (e.g., assay or system to determine an expression level of the reporter gene) and attached to a regulatory sequence triggered by an antigen presented by an accessory cell and encoding a protein, polypeptide, or enzyme capable of producing chemiluminescence when exposed to a substrate.

This invention provides a solution to the ongoing concern of using live animals as test matrices or sources of cells for the detection of microbial toxins. Systems and methods are disclosed where a cell line is engineered with a reporter gene expression system encoding a detectable protein, peptide, or enzyme expressed upon exposure to a microbial toxin. The protein, peptide, or enzyme is capable of producing luminescence upon addition of a substrate which is correlated to transcriptional activity of the reporter gene by operable linkage to a transcriptional regulatory region in response to microbial toxin exposure. The systems and methods have surprisingly superior quantitative properties which are economical, exceptionally sensitive, and conveniently implemented to detect microbial toxins in a variety of settings.

Figure 3A:
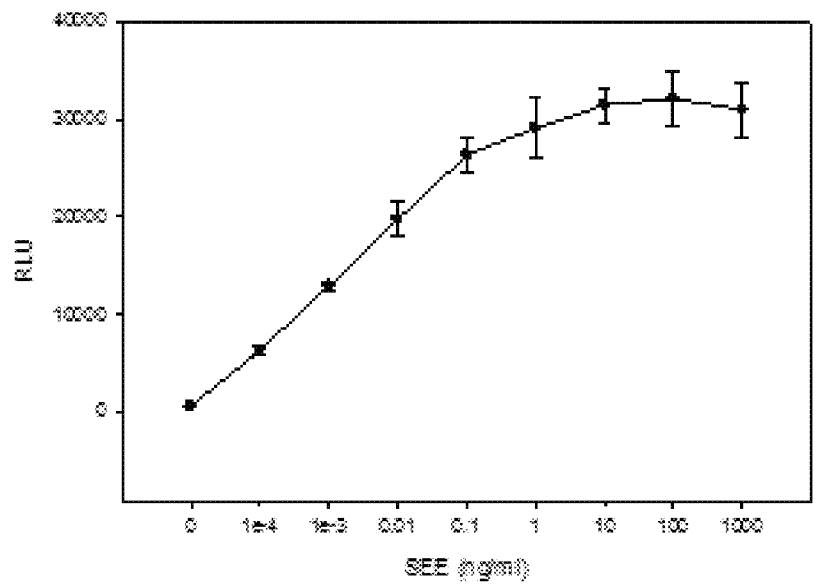
FIG. 3A-3B show examples of quantitative determination of the biological activity of microbial toxins by measuring light emitted from a reporter gene reaction.
Figure 3B:
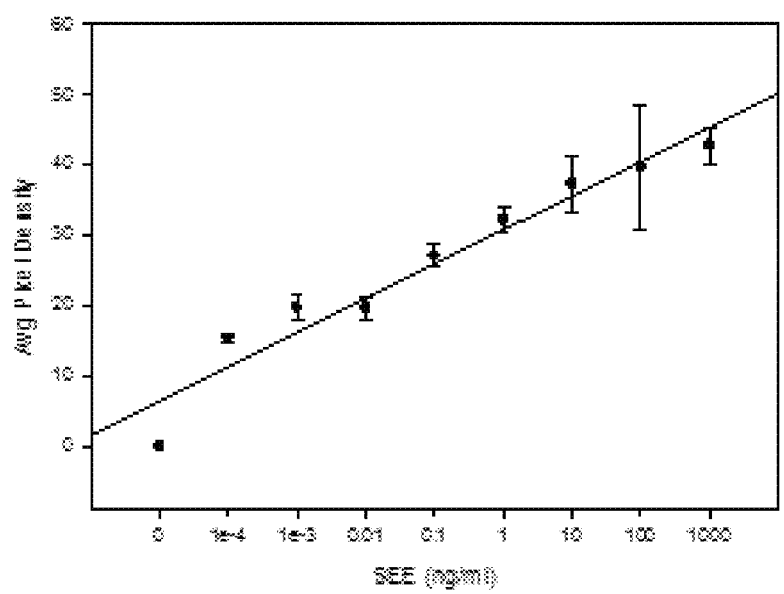
Figure 4:
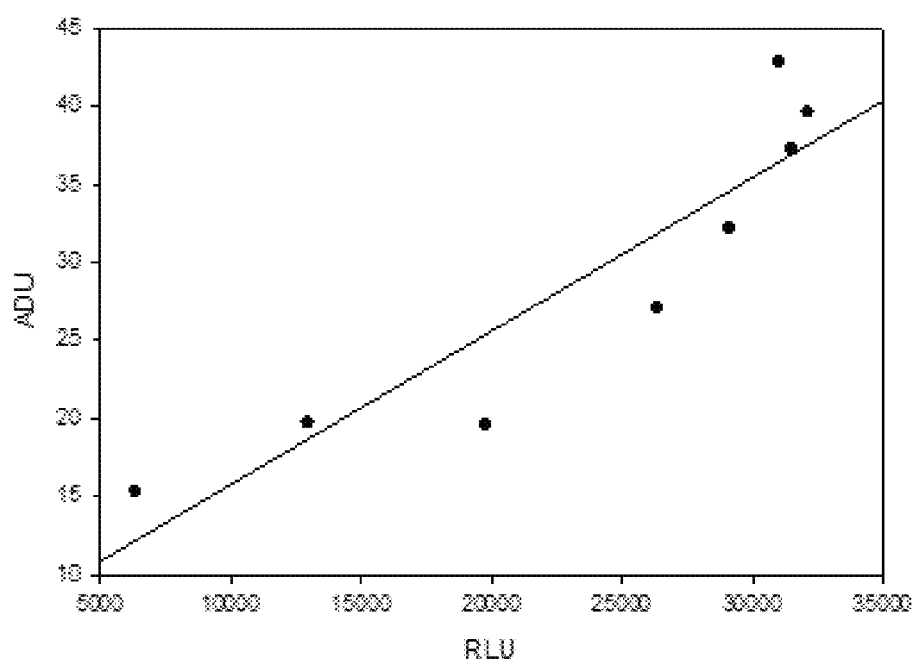
FIG. 4 shows an example of the correlation between the camera system of the invention and conventional plate reader measurements of microbial toxin activity expressed in units of ADU and RLU, respectively, where each data point corresponds to the same concentration of microbial toxin in the respective assays.
Figure 5A:
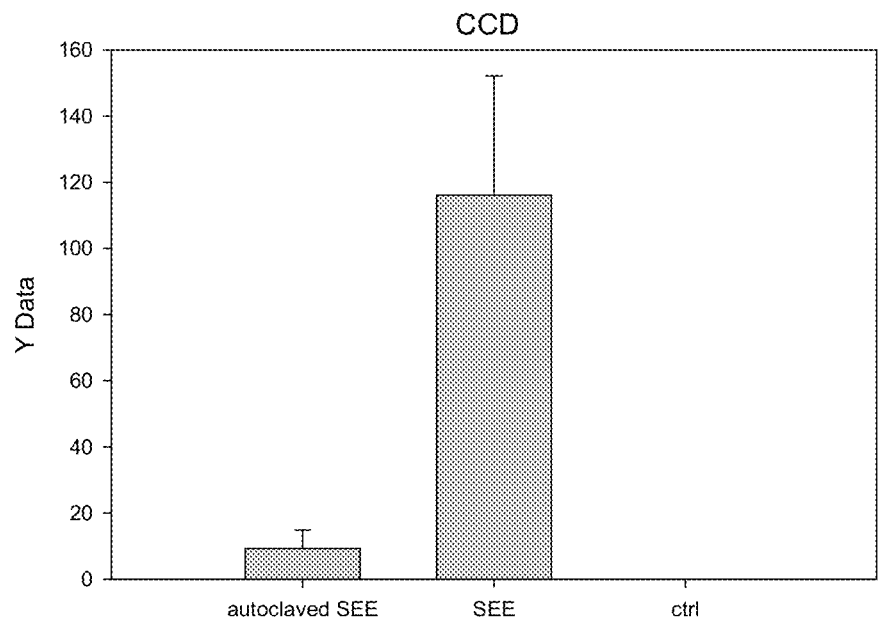
FIG. 5A-5C show examples of the correlation between active microbial toxin activity as compared to inactivated microbial toxin comparatively with the camera system of the invention and a conventional plate reader as quantified by image analysis software.
Figure 5B:
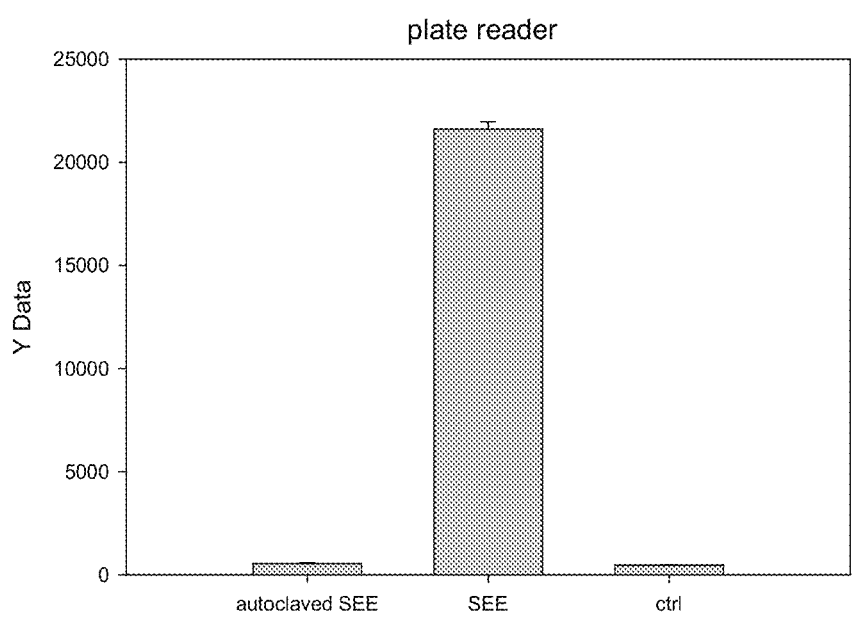
Figure 5C:
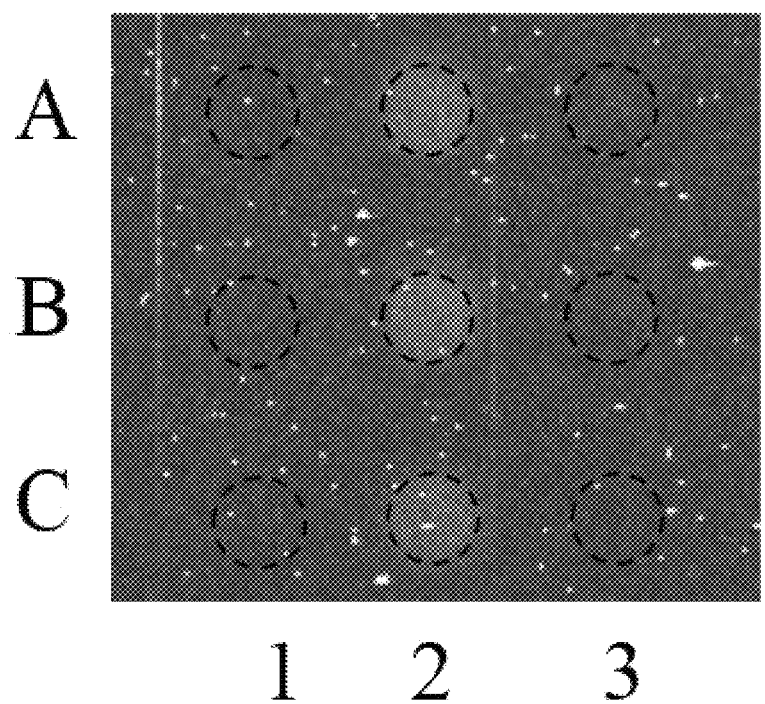

The disclosed systems and methods utilize direct or indirect microbial toxin stimulation of cell lines to trigger chemiluminescence detectable at previously unattainable low levels via an economical camera system. Applying the invention in this disclosure, it is possible to quickly (e.g., within about 2 to about 7 hours, or about 3 to about 6 hours, or about 4 to about 5 hours, or about 4.5 to about 5.5 hours) detect the presence of microbial toxins. The disclosed systems and methods are about one billion times more sensitive than a typical animal model and about one million times more sensitive than a typical ELISA-based assay as further discussed below. Cell lines are engineered to express a reporter gene upon direct or indirect exposure to a microbial toxin. Expression level of the reporter gene is correlated to the amount of microbial toxin present and creates a proportional chemiluminescent signal upon exposure to a substrate (e.g., FIGS. 3A and 3B illustrate linear log concentration response over the indicated concentration range as further discussed in the examples below). In embodiments, an accessory cell line may also be used to present the microbial toxin as an antigen on its surface as a major histocompatibility complex to the cell line engineered to express the reporter gene. The microbial toxin dose-dependent luminescence is captured by a camera device and the image analyzed to determine microbial toxin concentration. The disclosed systems and methods generally exhibit a dynamic range over 6-8 decades with a sensitivity from about 1 fg/mL to 100 fg/mL. The particular sensitivity and dynamic range are impacted by factors such as duration of the assay, exposure time, and camera/optical sensitivity as may be determined by a skilled artisan. It is also a surprising characteristic of the invention to effectively discern active microbial toxin from inactive toxin (e.g., toxin inactivated by autoclave treatment) in food matrices.

Referring to FIG. 1, system 100 is an embodiment of the invention showing imaging device 110, lens 120, analysis plate 130, well 140, and plate support 150. In embodiments, imaging device 110 is any suitable camera. For example, any camera using charge-coupled device (CCD) or complimentary metal-oxide-semiconductor (CMOS) image sensor may be used. Sensor resolution and image sharpness may vary among cameras and a suitable model having appropriate characteristics would be selected by a skilled artisan. In a preferred embodiment, camera 110 is a cooled CCD camera. To provide sufficient light sensitivity and image formation characteristics, a cooled camera is preferred for imaging device 110. The cooling function is advantageous because it reduces thermal noise and improves light sensitivity for enhanced image processing capabilities (e.g., for detection of low levels of microbial toxins or detection in hot ambient environments). Such cameras are commonly used for amateur astronomy. Though any camera cooling device may be used by a skilled artisan, an example of a common camera cooling system is a solid state thermoelectric cooling device. In embodiments, imaging device 110 is a non-cooled conventional camera which would be selected for cost considerations. As imaging technologies develop rapidly, new cameras with enhanced sensitivity (e.g., ability to detect low levels of chemiluminescence and, as such, low levels of microbial toxin), larger CCDs, and less thermal noise become available. Current examples of commercially available cameras include Atik 414EX (available from High Point Scientific, Montague, N.J.), Monochrome Starlight Xpress Trius SX-825 CCD (available from High Point Scientific, Montague, N.J.), SXVF-M7 (Adirondack Video Astronomy, Hudson Falls, N.Y.), Point Grey Research Chameleon (Audio Video Supply, Inc., San Diego, Calif.). It should be appreciated that any camera sufficient sensitivity as determined by a skilled artisan may be used in the systems and methods of the invention.

Lens 120 is preferably an interchangeable lens to allow customization of optical features such as focal distance and magnification. In embodiments, lens 120 is of fixed focal length and/or fixed magnification. In a preferred embodiment, lens 120 has an adjustable magnification and/or variable focal length. Lens 120 is a manual focus or automatic focus close-up macro lens (e.g., about 20 mm to about 50 mm focal length) according to embodiments. In preferred embodiments, lens 120 has a focal ratio (i.e., f-number or f-value) in the range of about 1.2 to about 5.8 and a focal length in the range of about 12 mm to about 80 mm. It should be appreciated that one having ordinary skill in the art may select an appropriate lens and imaging device combination dependent on the particular samples being measured. Imaging device 110 (e.g., camera) and lens 120 are selected to be compatible with each other and ensure satisfactory imaging and image capture. It should be appreciated that a skilled artisan may select a variety of different lenses for particular application of the invention, examples of available lenses include 12 Pentax f1.2, 25 mm Pentax F/1.4 M1 C-Mount (available from Spytown, Utopia, N.Y.). One with ordinary skill in the art should appreciate that these lenses are not microscope lenses are not lenses used or associated with microscopic systems or microscopes and have specifications to enable capturing a field of view as large as those shown in the examples below. Alternatively, or in conjunction with lens 120, a secondary lens (e.g., close-up filter, close-up lens, macro filter, fish-eye lens, wide angle adaptor, and the like) may also be incorporated by a skilled artisan to ensure sufficient sensitivity of the image captured by the imaging device 110. Examples of available secondary lenses include extension tubes of 1 mm, 5 mm, 10 mm, 20 mm, or 40 mm length (Spytown, Utopia N.Y.) and Vivitar Close-Up Lens Set (B&H Photo, NY, N.Y.)

Analysis plate 130 may be any apparatus capable of holding a volume of sample suitable for the disclosed systems and methods. In a preferred embodiment, analysis plate 130 is opaque (e.g., black or dark in color) or essentially opaque to allow the luminescence within well 140 (or within each of a plurality of wells 140) to be more accurately detected by imaging device 110. The optical properties of the sides of well 140 should also prevent light conductance between wells when more than one well 140 is present to ensure each well is measured independently of other wells and to maintain accuracy. In embodiments, analysis plate 130 is a standard 96 well plate (where well 140 of FIG. 1 represents one of the 96 wells) with optional support 150. Analysis plate 130 in conjunction with optional support 150 must be positioned at a distance and in a manner to allow well 140 to be within the focal plane of imaging device 110. In embodiments, analysis plate 130 does not use support 150 or has an integrated support 150 for positioning analysis plate 130 such that well 140 is within the focal distance of imaging device 110. In other embodiments, analysis plate 130 is a custom-designed plate with at least one well 140 and compatible with optional support 150. In embodiments, the volume of the wells is in the range of about 20 µL to about 200 µL. The particular volume needed for an application of the invention depends upon the particular sample set and may be ascertained and implemented by a skilled artisan.

In embodiments, a food matrix suspected of having an amount of microbial toxin is used as a sample. Such food matrices may be solid or semi-solid as well as liquid or gel. The food matrix may be prepared using any methods known in the art. For example, the food matrix may be homogenized, filtered, macerated, diluted, concentrated, etc. It should be appreciated that in some cases there is uncertainty of the presence (or lack thereof) of confounding or interfering substances in food matrices. Therefore, it is preferred to first isolate the microbial toxin component from the food matrix by application of methods known in the art for such isolations. For example, an effective method is the use of immunomagnetic beads (see e.g., Rasooly, R & Do, P. M., 2008, Development of an In Vitro Activity Assay as an Alternative to the Mouse Bioassay for *Clostridium botulinum* Neurotoxin Type A Appl Environ Microbiol, 2008 July 74(14):4309-13). The toxin is eluted from such beads and the resulting sample suspected of containing an amount of microbial toxin is then subjected to the methods of the invention.

Cell lines for use in the present invention have a reporter gene construct that express an enzyme capable of producing a luminescent signal suitable for cell imaging via a regulatory sequence in proportional response to the presence of a microbial toxin. It should be appreciated that a skilled artisan may select any suitable cell line, preferably a stable cell line, having a suitable reporter gene construct for use in the disclosed invention. A preferred reporter gene is one that encodes an enzyme which exhibits a luminescent or fluorescent signal. The luciferase enzyme is preferred. In other embodiments, reporter genes expressing, for example, green fluorescent protein (GFP), blue fluorescent protein (BFP), β-Galactosidase, or the like may be used. One advantage of using luminescent or fluorescent signals (as compared to colorimetric signals) is the ability to increase exposure time to compensate for a lower signal. The optics would be modified according to the particular reporter used as determined by a skilled artisan. Luciferases, for example, make up a class of oxidative enzymes found in several species that enable the organisms that express them to "bioluminesce" or emit light. The most common one of these enzymes is the firefly luciferase. Fireflies are able to emit light via a chemical reaction in which luciferin is converted to oxyluciferin by the luciferase enzyme. Some of the energy released by this reaction is in the form of light. This reaction was surprisingly and unexpectedly found to be extremely sensitive to the presence of microbial toxins in the systems and methods of the invention as a quantitative means of determining low levels of active microbial toxins. The reporter gene is typically expressed via activation of a regulatory sequence. The activation of the regulatory sequence in T cells, for example, is commonly triggered by a transcription element such as the nuclear factor of activated T-cells (NFAT) response element (see e.g., Rao, A., et al., Transcription Factors of the NFAT Family: Regulation and Function, Annu. Rev. Immunol. 1997. 15:707-47).

The reporter gene encodes an enzyme capable of reacting with a substrate to produce a chemiluminescent (e.g., bioluminescent, fluorescent) signal detectable through system 100. In embodiments, the cell line is a genetically engineered stable T-cell line (e.g., Jurkat T-cell line) expressing a luciferase reporter gene under the regulation of NFAT response element (NFAT-RE). It should be appreciated that the response element used is not critical and may be selected by a skilled artisan for a particular application. In embodiments, an accessory cell is used to present the microbial toxin via a major histocompatibility complex (e.g., MHC class I and/or II complexes) to the engineered T-cell line. Example of suitable accessory cells (see e.g., Hume D A, Macrophages as APC and the dendritic cell myth. J Immunol. 2008 Nov. 1 181(9):5829-35. Review; Théry C & Amigorena S, The cell biology of antigen presentation in dendritic cells. Curr Opin Immunol. 2001 Feb. 13(1):45-51. Review) include stable B-cell lines (e.g., American Type Culture Collection, Manassas, Va. (ATCC) #CCL-86), macrophages (isolated, for example, using #130-091-153 from Miltenyi Biotec), and dendritic cells (e.g., ATCC #CC-2701). Exposure of a mixed culture of T-cells and B-cells to increasing microbial toxin concentrations induces differential expression of the luciferase reporter gene and bioluminescence in a dose-dependent manner over a range of about 6-8 logs (e.g., about 6-8 decades or 6-8 decades) in an exemplary embodiment. A greater dynamic range of response is advantageous. In some cases, the dynamic range is limited by factors inherent in the assay system. For example, a dim reporter (e.g., a dim reporter is a reporter molecule with low luminescence intensity, low fluorescence, or low colorimetric extinction) will likely exhibit limited dynamic range because at low response levels the signal will be masked by noise even if the cellular reporter is sensitive to low levels of toxin. The lower limit of detection is a factor of the cell-based reporter to respond to low levels of toxin. This limit will vary according to the toxin to be detected and the particular cellular reporter used. For example, the lower limit of detection of biologically active SEE was surprisingly found to be about 1 fg/mL (as discussed in the examples below), which is $10^4$ times more sensitive than a typical spleen cell proliferation assay (see e.g., Rasooly R. & Do P. M., In vitro cell-based assay for activity analysis of staphylococcal enterotoxin A in food, FEMS Immunol Med Microbiol. 2009 July; 56(2):172-8), about $10^6$ times more sensitive than a typical ELISA-based assay (see e.g., Bennett R. W., 2005, Staphylococcal enterotoxin and its rapid identification in foods by enzyme-linked immunosorbent assay-based methodology, J Food Prot 68(6):1264-70; Dupuis A., et al., 2008, Protein Standard Absolute Quantification (PSAQ) for improved investigation of staphylococcal food poisoning outbreaks, Proteomics 8(22):4633-6), and about $10^9$ times more sensitive than an animal model assay (e.g., monkey or kitten; see e.g., Bergdoll M. S., 1988, Monkey feeding test for staphylococcal enterotoxin. Methods Enzymo 1165:324-33; Bergdoll M. S., et al., 1971, Identification of enterotoxin E. Infect Immun 4(5):593-5).

It should be appreciated that many different cell lines (e.g., commercially available stable cell lines, custom cell lines, etc.) are suitable for use in the systems and methods of the invention as determined by one of ordinary skill in the art. Cell lines enhanced with the reporter genes for use in the invention are typically engineered (e.g., transformed, transfected, cloned) with an expression system capable of producing a chemiluminescent signal detectable by an imaging device (e.g., camera). Reporter gene constructs may be synthesized using known methods by a person of ordinary skill in the art. Commercially available examples of reporter gene constructs for use in the invention include bacterial Lac-Z DNA sequence from a pVS-b-galactosidase plasmid vector (Promega, Madison, Wis.) and the Firefly Luciferase sequence from pGL3-Basic Vector (Promega) for the production of custom cell lines by a skilled artisan. The cells may be primary transfectants, transformants, clones, etc. or maintained stable cell lines. Many methods of engineering cells with an expression system or expression cassette compatible with the systems and methods of the invention are known in the art, including, for example, reagent-based methods (e.g., lipids, calcium phosphate, polymers, dendrimers, magnetic beads), mechanical methods (e.g., electroporation, microinjection, ballistics, lasers), and viral methods.

Figure 6A:
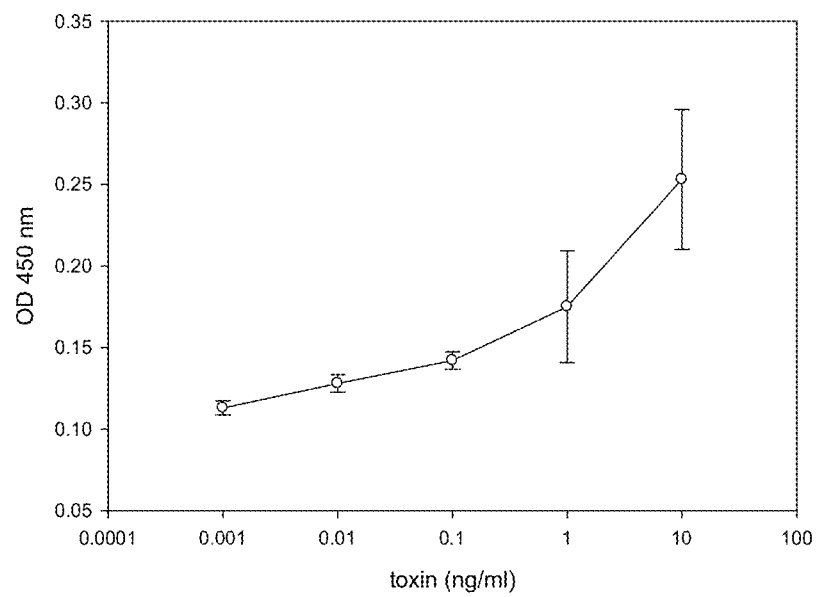
FIG. 6A-6B show examples of the quantitative determination of microbial toxin concentration comparatively with the camera system of the invention and a conventional plate reader in food matrices including white grape juice, peach mango juice, and apple cider.
Figure 6B:
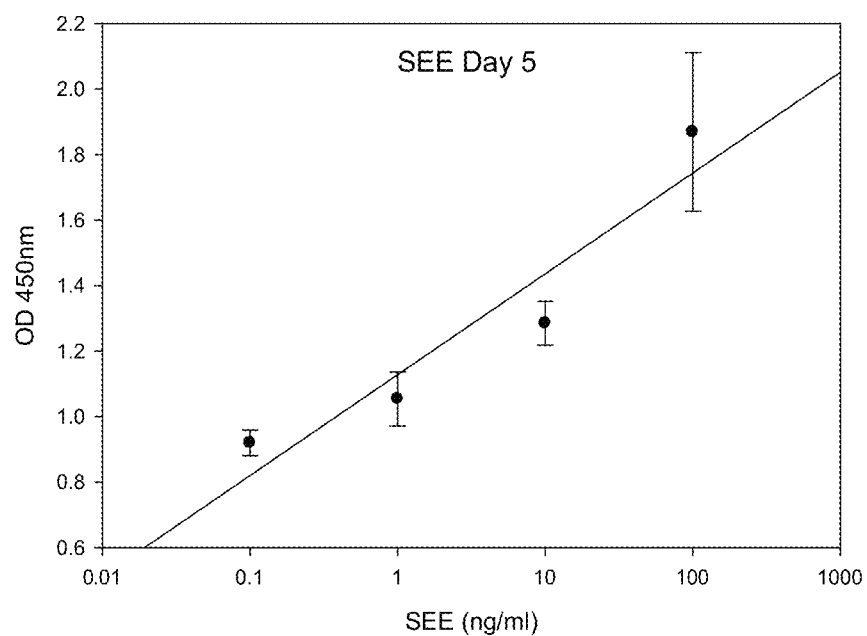

In embodiments, a cell line is capable of multiple functionality. For example, a subtype of mouse naïve CD4+ T cells expresses MHC class II on their cell surface, and are also capable of expressing a reporter gene (see e.g., Rasooly, R., et al., Auto-presentation of Staphylococcal enterotoxin A by mouse CD4+ T cells. Open J. Immunol. 2011, 1, 8-14). In other embodiments, an antigen presenting cell line (e.g., Raji cell line, B-cell lymphoma line) presents an antigen on its surface and a transformed cell line (e.g., T-cell such as Jurkat T-cell line) having a reporter gene expression system. For example, activation of an immune response begins with the binding of microbial toxin by the major histocompatibility complex (MHC) class II expressed on the surface of antigen presenting cells. Once bound, the molecule is presented to T-cells (see e.g., Alberts B., et al., 2002, Molecular Biology of the Cell. 4th edition. New York: Garland Science; T Cells and MHC Proteins. Available from: www.ncbi.nlm.nih.gov/books/NBK26926) which also bear receptors that bind and recognize the microbial toxin via specific sequences (e.g., TcR Vβ chain domains; costimulatory CD28; see e.g., Arad G. et al., 2011, Binding of Superantigen Toxins into the CD28 Homodimer Interface Is Essential for Induction of Cytokine Genes That Mediate Lethal Shock, PLoS Biol 9(9): e1001149. doi:10.1371/journal.pbio.1001149). In another example, an adjunct B-cell line (e.g., Raji B-cell line) is used to present the microbial toxin antigen on its surface which, in turn, activates a genetically engineered Jurkat T-cell line (e.g., Promega, J1601; BPS Bioscience (San Diego, Calif.), 60621; Signosis (Santa Clara, Calif.), SL-0032; Amsbio (Cambridge, Mass.), 60621; Invivogen (San Diego, Calif.), jktl-nfat). A reporter gene (e.g., encoding luciferase) is under regulation of a response element such as, for example, the NFAT response element (NFAT-RE). Not wishing to be bound to a particular theory, it is thought that certain microbial toxins may have specificity for certain response elements (e.g., TcR alleles TRAV84, TRAJ3 and TRBV123, TRBJ12 that may bind to SEA, SED, and SEE), whereas others may be less specific and react to a variety of microbial toxins. In some cases, the disclosed system may exhibit a degree of non-specificity for various microbial toxins (e.g., SE subtypes, other toxins, contaminants) which is usually not desirable. However, it is possible to add a step to the sample preparation process to specifically isolate the target microbial toxin from the sample matrix by using antibodies specific for the toxin of interest (e.g., via immunomagnetic beads as discussed herein). Therefore, if there are contaminating toxins or other molecules that produce a non-specific response, those contaminants will be greatly diminished by this added step.

The image captured with system 100 is transmitted and analyzed via image processing equipment and software. In embodiments, data analysis software such as, for example, ImageJ (available from imagej.nih.gov/ij/), Icy (available from icy.bioimageanalysis.org), Image Pro by Media Pro cybernetics (available from www.mediacy.com/imagepro-plus), Fiji image (available from fiji.sc/Fiji), Avizo Fire (available from www.fei.com/software/avizo-3d-for-materials-science), OpenCV (available from opencv.org), Matlab (available from www.mathworks.com), TissueQuant (available from www.ncbi.nlm.nih.gov/pubmed/21924792), VV (available from www.creatis.insa-lyon.fr/rio/vv), Resemble.js: Image analysis and comparison (available from huddle.github.io/Resemble.js), CellProfiler Analyst (available from bmcbioinformatics.biomedcentral.com/articles/10.1186/1471-2105-9-482) for signal quantitation and data presentation is used as selected by a skilled artisan. The software begins with an image file and applies a gate to a specific region of the image (a circle, for example, with circular wells, see FIG. 5C) and averages all the pixel intensities within that gate/region. When multiple images are analyzed, the averages from each image are further averaged. Such averaged pixel intensities are then correlated to microbial toxin concentrations in the samples.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement. The following examples are intended only to further illustrate the invention and are not intended in any way to limit the scope of the invention as defined by the claims.

Example 1

Materials and Methods

Materials. Analysis plates having 9 wells and constructed of ⅛" thick black poly(methyl methacrylate) (PMMA), thin polycarbonate sheeting, and double-sided adhesive transfer tape (available from 3M, under item #9770), were obtained from Piedmont Plastics, Inc., Beltsville, Md. The plates used in this example were constructed from the above materials using a laser cutter. The volume of each well was about 30 μL. The diameter and depth of the wells can be varied to suit the application. Also, conventional multi-well plates can be substituted. SEE toxin was purchased from Toxin Technology, Sarasota, Fla. Inactivated SEE was prepared by autoclaving the SEE toxin for 30 minutes at 121° C. Media reagents; RPMI 1640, fetal calf serum (FCS), MEM nonessential amino acids, sodium pyruvate, hygromycin B, and penicillin/streptomycin, were purchased from Gibco/Invitrogen, Carlsbad, Calif. Bio-Glo reagent was obtained from Promega Sunnyvale, Calif.

Cell Lines and Culture. Raji B cell line (Burkitt's lymphoma ATTC #CCL-86) was obtained from the American Type Culture Collection, Rockville, Md. A Jurkat cell line (T cell leukemia) genetically modified for stable expression of the luciferase reporter gene under control of NFAT response element was obtained from Promega, Sunnyvale, Calif. RPMI 1640 containing 10% FCS, 1% MEM nonessential amino acids and 100 nM sodium pyruvate was used as basic cell culture medium and further supplemented with 200 μg/mL hygromycin B for Jurkat cells or with 100 units/mL penicillin and 100 μg/mL streptomycin for Raji cells. Cells were cultured in a 37° C. incubator under a humidified 5% $CO_2$ atmosphere (see e.g., Rasooly, R., et al., Rapid Cell-Based Assay for Detection and Quantification of Active Staphylococcal Enterotoxin Type D. J Food Sci. 2017 March; 82(3):718-723. doi: 10.1111/1750-3841.13634. Epub 2017 Jan. 30).

Photo Detector Apparatus. The photodetection device was comprised of a 16-bit greyscale cooled CCD camera and a custom fabricated assay plate (described above). The camera was an astronomical model SXVF-M7 (Adirondack Video Astronomy, Hudson Falls, N.Y.), to which was mounted a 12 mm f1.2 lens (Spytown, Utopia, N.Y.). Assay plates were laser machined from black PMMA sheet to which 3M 9770 adhesive transfer tape was attached to one surface. Wells were laser machined as straight through round holes. Attachment of a thin polycarbonate sheet to the side of the plate with adhesive completed the formation of the wells. The use of black PMMA material absorbs ambient light and also reduces the transfer of light between wells.

Image Processing. The camera used to capture images incorporated a semiconductor charge-coupled device (CCD), which converts incident photon energy into an electric signal to digitize the images for image processing. The astronomical cooled CCD SXVF-M7 camera was used for its high quantum efficiency and response linearity, as well as its ability to generate high-quality, low noise images. The images were analyzed and the photon signal intensity quantified with ImageJ (see e.g., Rueden, C. T. & Eliceiri, K. W., 2007. BioTechniques 43 (1 Suppl), S33-S36). The average sensor background signal was subtracted from sample images. This background signal was recorded by capturing images with exposure and gain settings identical to those used to image samples. Each data point was calculated as the mean pixel intensity value represented by a digital number in three samples. Statistical analysis was performed with SigmaStat 3.5 for Windows (Systat Software, San Jose, Calif.). ANOVA was used to determine the limit of detection for SEE. The experiments were repeated at least 3 times, and results with $P<0.05$ were considered statistically significant. The error bars represent the statistical error of the mean pixel intensity.

Microbial Toxin Assay. To detect and quantify microbial toxin (streptococcal enterotoxin subtype E (SEE) in this example), samples were incubated with Raji cells and Jurkat reporter cells in black 96 well microplates with clear bottoms. Each well contained $1\times10^5$ Jurkat cells in a 50 μL volume without hygromycin B and $5\times10^4$ Raji cells in a 25 μL volume plus a 25 μL sample containing SEE such that the final SEE concentration in the assay was ¼ the initial concentration in the sample or stock solution. The incubation period was 5 hours at 37° C. followed by a 10 to 15 minute equilibration to room temperature. 100 μL BIO- GLO™ Luciferase Assay System (a luciferase activity detection reagent available from Promega, Madison, Wis.) was added per well followed by a 5 to 10 minute incubation period at room temperature to detect luciferase expressed by the Jurkat reporter cells in response to the presence of various concentrations of SEE. The luciferase enzyme activity was detected according to the BIO-GLO Luciferase Assay System manufacturer's instructions. After incubation the plate was brought to room temperature. The assay buffer was mixed with the substrate and 100 μL of the substrate was pipetted into each well. After 15 minutes, the wells were read in a luminometer plate reader or the CCD camera. Luminescence was quantified per well using either a commercial plate reader or the photo detector apparatus. In the latter case, 80 μL of the reaction mixture was transferred from each well of the 96 well plate to wells in a custom analysis plate constructed as described above, and analyzed accordingly Results Quantitative Bioluminescence Assay for Measuring Biologically Active Microbial Toxin. Experiments were performed to test the suitability of CCD camera imaging for quantification of the chemiluminescence (e.g., bioluminescence) response of Jurkat cells genetically engineered to express firefly luciferase as a reporter gene for microbial toxin detection. Concentrations of SEE from 100 ng/mL to 100 fg/mL were applied to the bioassay mixture of Jurkat and Raji cells and after 5 hour incubation the assay sample mixture was diluted 4:1 and transferred to 9-well sample plates as described above (FIG. 2 well C1, 100 ng/mL—FIG. 2 well A3, 100 fg/mL). The Point Grey Research astronomy CCD camera was first used to quantify the light intensity from the luciferase-catalyzed luciferin (e.g., Bio-glo as discussed above) reaction. With this camera, however, the signal levels of the cellular luminescence were too low to be discerned against the background. Leaving the shutter open for longer light exposure permitted an increase in signal but also increased the thermal noise generated within the silicon structure of the CCD. The 16-bit grayscale, astronomical cooled CCD SXVF-M7 camera equipped with Pentax 12 mm f1.2 lens was selected to address this problem because it was cost effective and easily obtainable. Photon intensity was detected by converting photons carrying sample image information into an electronic signal after striking silicon wafers to generate an image. The CCD chip was cooled to reduce the background thermal noise (in general, the greater the degree of cooling the more that thermal noise can be reduced). FIG. 2 shows an example image of the 9-well custom assay plate in which the CCD cooling reduced the noise and improved the sensitivity of the assay. An uncooled camera was used in a series of experiments, but the background noise was too great to distinguish useable data (not shown). Increased light intensity level corresponded to increased SEE concentration with dose dependency.

Detection limit comparison of microbial toxin using CCD measurements and plate reader. The average light signal intensity of each pixel from three images was quantified by free imaging software ImageJ (see e.g., Rueden, C. T. & Eliceiri, K. W., 2007, Visualization approaches for multidimensional biological image data. BioTechniques 43(1 Suppl):31, 3-6). The average background signal was subtracted from the sample images and the optical brightness intensity reported in analog-digital units (ADU) plotted against SEE concentrations. FIG. 3A shows that the light intensity is proportional to SEE concentration over an 8-log range with linear correlation $R^2$=0.98. In terms of sensitivity, as illustrated in FIG. 3A the system of the present invention surprisingly and unexpectedly enables the detection of less than 100 fg/mL of biologically active SEE. The procedure was replicated using the same range of toxin concentrations except that the samples were placed in a 96-well plate and the luminescence was measured using a commercial plate reader. As seen in FIG. 3B, this data showed a similar dose-dependent response although with impaired linearity at higher toxin concentrations. Adding SEE at concentrations greater than 0.1 ng/ml resulted in high illumination levels that saturated the plate reader sensor. As a result, an increase in light intensity at higher toxin concentrations produces no further change in recorded signal.

Relationship between plate reader and CCD measurements. The correlation between CCD and plate reader responses was determined by plotting the respective data from one device against the other over the range of SEE concentrations employed. FIG. 4 shows the CCD response (y-axis) versus the plate reader response (x-axis). With a linear fit, the degree of agreement between the two devices produced a coefficient of determination $R^2$=0.84. Deviation from linearity at the high response end is due to saturation of the plate reader. The results demonstrate that the simple CCD sensor apparatus is a suitable and effective detector demonstrating surprising sensitivity in combination with this bioassay for active SEE toxin as compared to a conventional plate reader.

Bioluminescence assay that differentiates between active and inactive microbial toxin. To assess microbial toxin deactivation and to discern active microbial toxin, which poses a threat to public health, and inactive microbial toxin, which exhibits no toxicity, the assay must respond selectively to active microbial toxin and not just to the presence of the toxin molecule. Presently, the accepted assays for microbial toxin activity are the emetic response bioassays using live monkeys or kittens fed or injected samples containing microbial toxin. These methods are both expensive and undesirable from an ethical standpoint, particularly in light of growing regulatory pressure to use alternatives to animal testing. To test the ability of the disclosed system to discern active from inactivated microbial toxin, samples of SEE were autoclaved for 45 minutes to denature the molecule and compared to SEE samples without autoclave treatment. FIG. 5A-5C shows example images from the photo apparatus (FIG. 5A) and plots of bioluminescence intensity from triplicate tests read with the photo apparatus (FIG. 5B) and with a plate reader (FIG. 5C). The photo shows that the luciferase reaction generated light only in the wells with active SEE (wells C2, B2, and A2). The autoclaved SEE samples in wells C1, B1, and A1 elicited no light production, comparable to the control wells lacking SEE (wells C3, B3, and A3). This demonstrates the applicability of this low cost imaging apparatus for measurement of biologically active microbial toxins using the genetically engineered cell-based assay of the invention.

Detection of active microbial toxin in a food matrix. To evaluate the ability of the assay to detect microbial toxin in food matrixes, white grape juice, peach mango juice, and apple cider were spiked with SEE. The result in FIG. 6A shows that by using the system of the invention differences between spiked and unspiked juice are detectable. The light emitted from spiked juice was significantly higher than the light emitted from unspiked juice. This result was validated using a luminometer (FIG. 6B).

Example 2

Figure 7A:
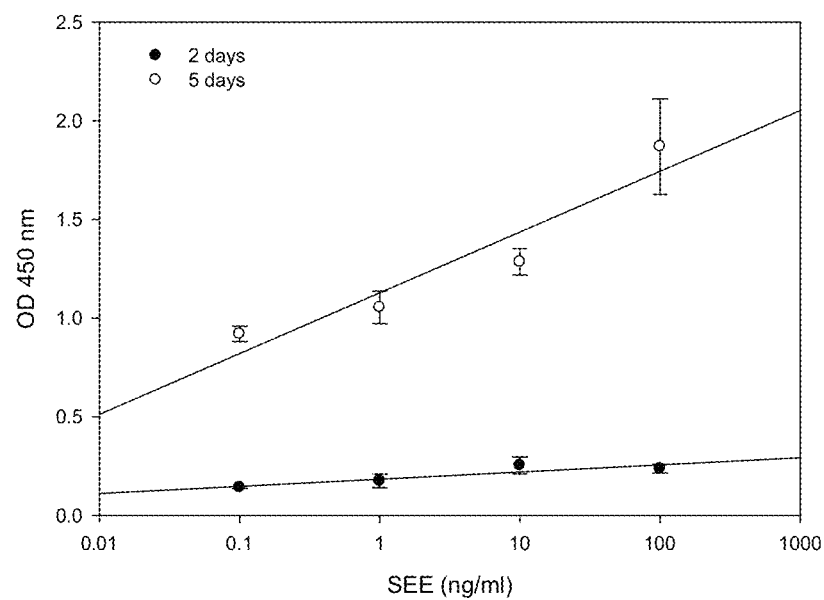
FIG. 7A-7B illustrates comparisons of the detection of microbial toxin by spleen cell proliferation assay or by cell line-based assay.
Figure 7B:
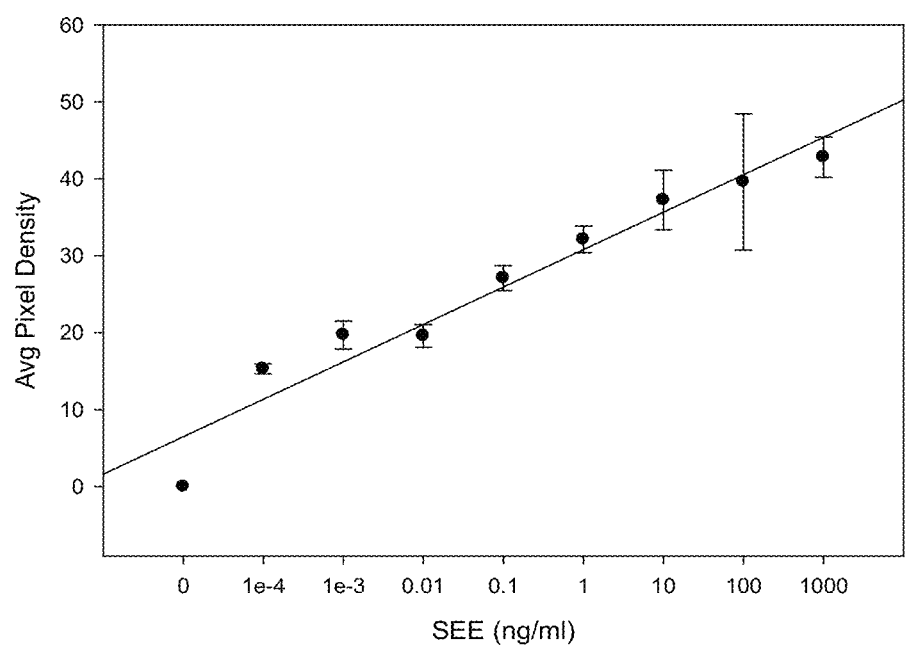

To measure the biological activities of SEE, a Jurkat T-cell reporter cell line in combination with Raji cells that perform the role of APC and present the SEE-MHC class II complex to the Jurkat T cell line was used. FIG. 7B shows that the light intensity is proportional to SEE concentration over an 8-log range with linear correlation $R^2=0.98$. This result was compared with Murine splenocyte proliferation assay that required the sacrifice of live animals. In terms of sensitivity, this Jurkat cell line-based assay enables the detection of less than 100 fg/mL of biologically active SEE, an amount which is $10^4$ times more sensitive than the proliferation bioassay at a detection limit of 10 ng/mL. This cell line assay of the invention is surprisingly sensitive, fast, simple, and inexpensive alternative to the ex vivo bioassay. An expected result would have been that because the splenocyte population contains a variety of antigen-presenting cells and a variety of T cells with different specificities to antigens, that the sensitivity would be high relative to the present case with only one antigen-presenting cell line and one clonal population of T cells with only one type of T cell receptor. Surprisingly, a much higher sensitivity was observed using the methods of the invention.

Example 3

Figure 8:
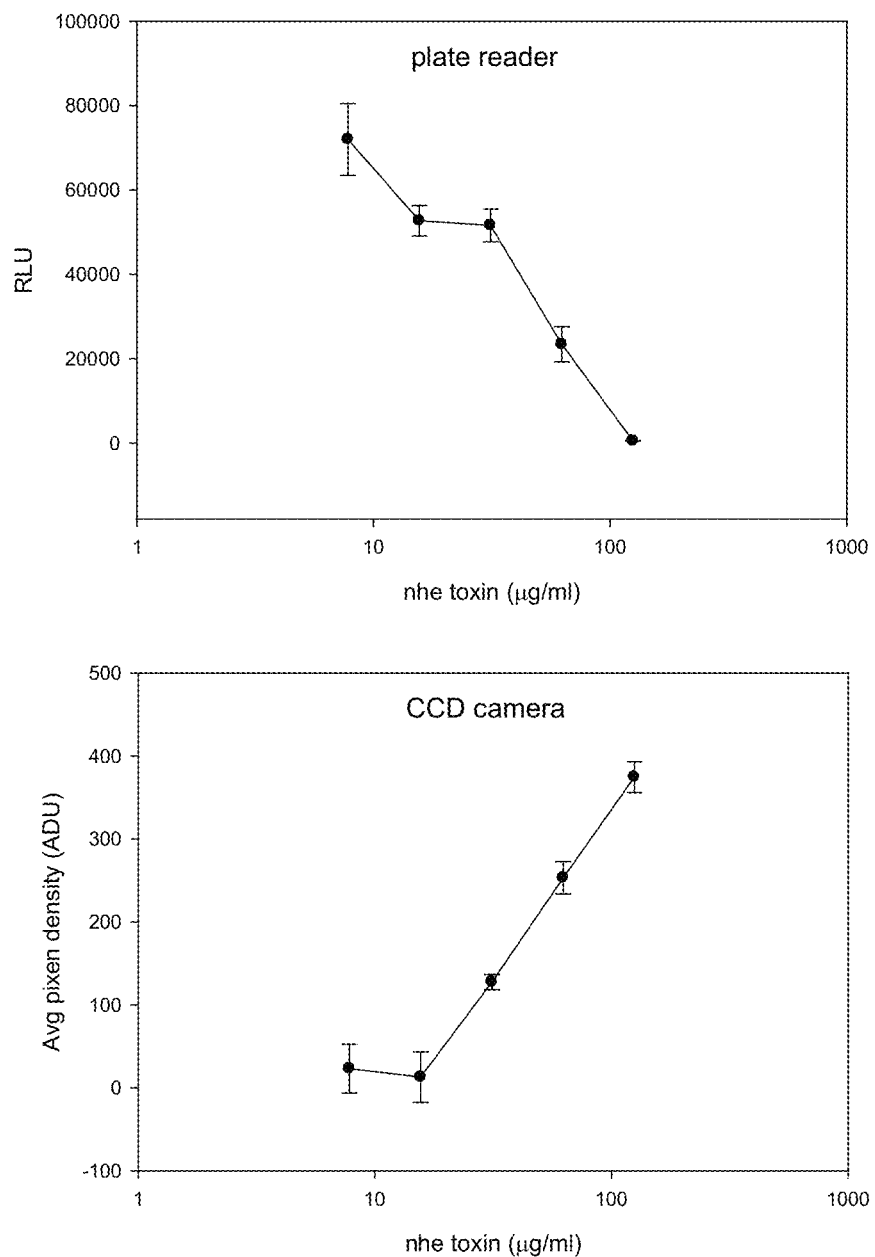
FIG. 8 shows an example of the ability of the disclosed system to detect non-haemolytic enterotoxin (Nhe) from the bacterium *Bacillus cereus*.
Figure 9:
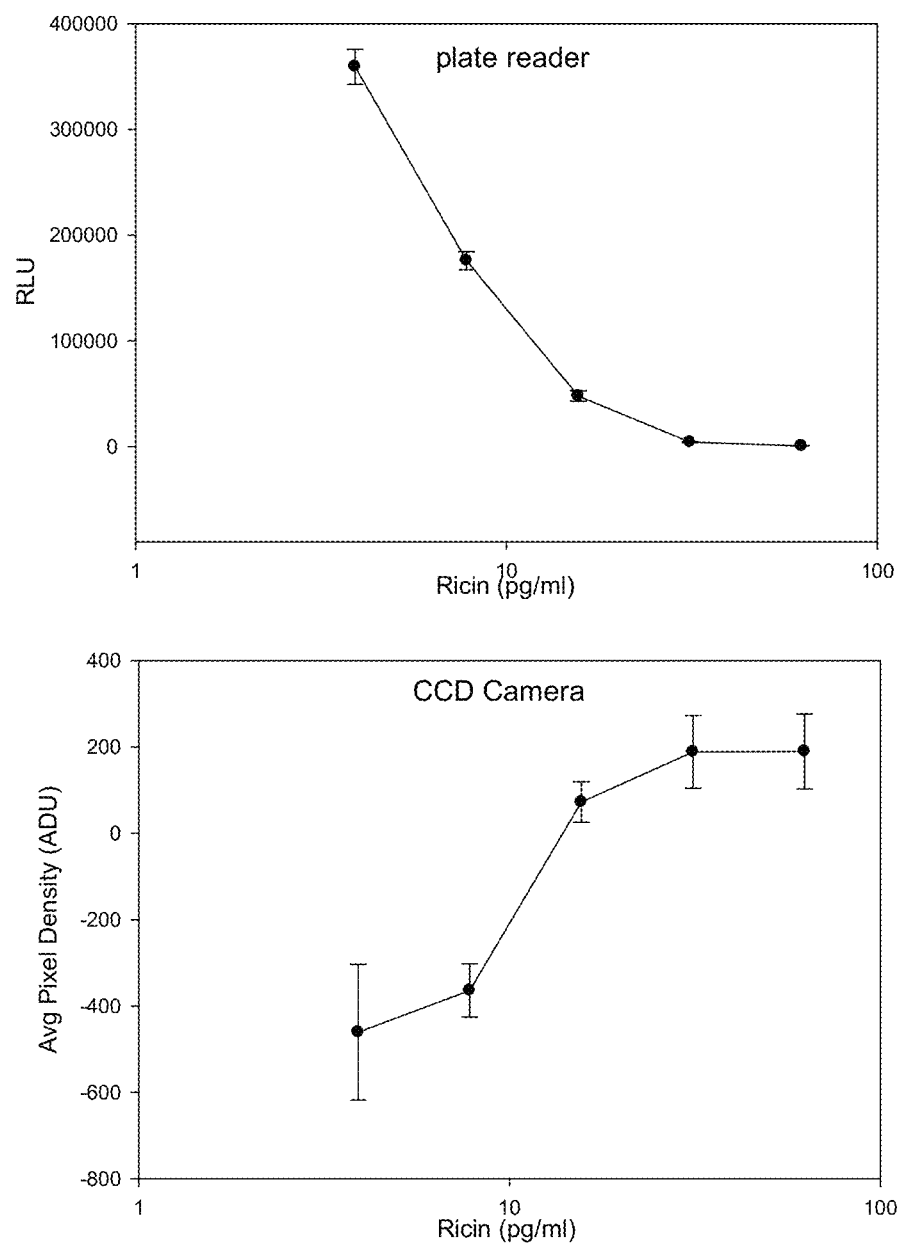
FIG. 9 shows an example of the ability of the disclosed system to detect the microbial toxin ricin from Castor bean.
Figure 10:
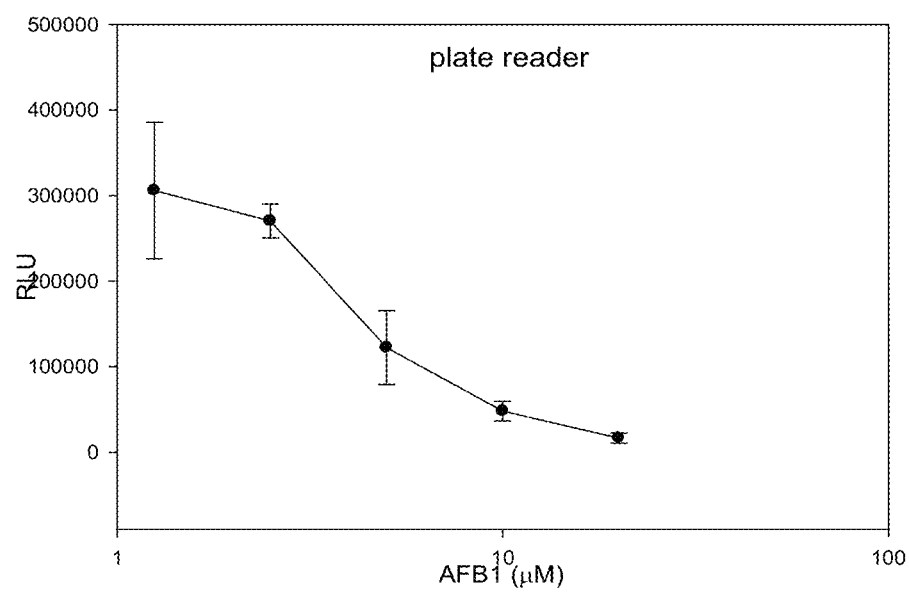
FIG. 10 shows an example of the ability of the disclosed system to detect the microbial toxin Aflatoxin B1 from *Aspergillus* sp.
Figure 10:
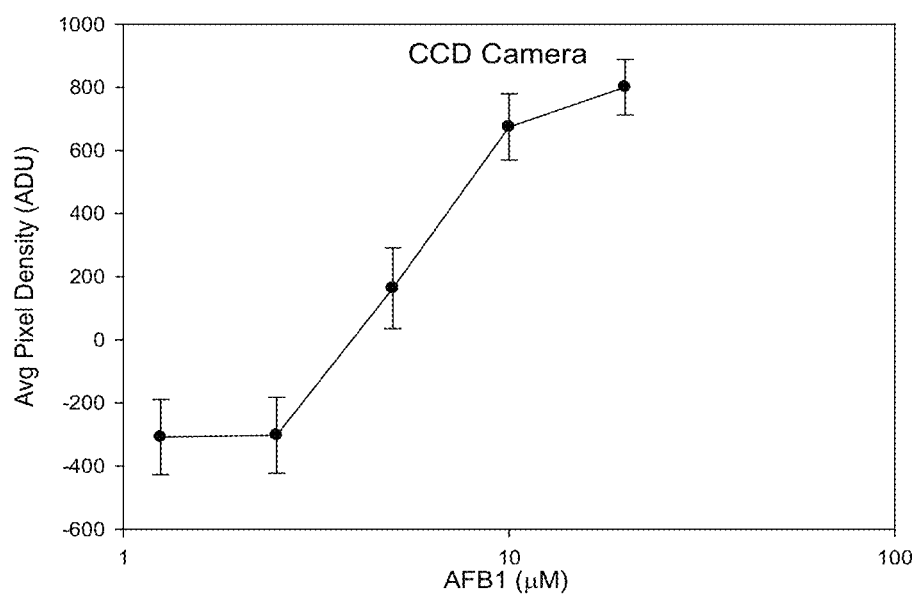

In this example, the ability of the disclosed system to detect other type of microbial toxins using different cell lines was tested to compare a conventional plate reader versus the imaging device of the present invention. As a reporter construct, a CMV vector was constructed with the gene for firefly luciferase and a CMV-Luc promoter (details of the constructs and procedure are available in the following reference with the exception that the assay was adapted to analysis by using the present invention: Rasooly R, et al., 2013, Low Levels of Aflatoxin B1, Ricin, and Milk Enhance Recombinant Protein Production in Mammalian Cells. PLoS ONE 8(8): e71682. doi:10.1371/journal.pone.0071682). This reference required the use of bright field light microscopic analysis to visually show the enhanced expression of the recombinant protein β-galactosidase used in the published study. In part, adapting the assay for the present invention included the use of a system and components as disclosed herein that is not part of a microscopic system and does not utilize a microscope or a microscope lens. Each cell line was transduced with the viral vector and incubated with the toxin for 3 days. Luciferase substrate was added to the cell suspension according to the Promega protocol and the luminescence analyzed as before. FIG. 8 shows results from non-haemolytic enterotoxin (Nhe) from the bacterium *Bacillus cereus* tested using Vero cells. FIG. 9 shows results for Vero cells treated with the microbial toxin ricin from Castor bean. FIG. 10 shows results for Vero cells treated with the microbial toxin Aflatoxin B1 from *Aspergillus* sp. FIG. 11 shows results for Vero cells treated with the microbial toxin Abrin from *Abrus precatorius* (imaging device results only).

DISCUSSION

The examples demonstrate the inexpensive, rapid, and highly sensitive methods for detecting and quantifying active microbial toxins that do not require the use of live animals. The combination of these results and knowledge permitted the development of an animal-free cell based assay, the key components of which were an accessory cell (e.g., B-cell line (such as Raji B-cell line) to bind and present the SE molecule through its MHC class II peptide binding motif and a specially genetically engineered T cell line (e.g., Jurkat cell line) that incorporates a reporter gene controlled by a regulatory sequence. The resultant assay is a rapid and inexpensive alternative to the expensive live animal emetic monkey or kitten assays which have the additional disadvantage of limited use in only a few laboratories with the necessary facilities. The data presented here show that a low cost cooled imaging devices (e.g., CCD cameras) initially designed for other purposes (e.g., astrophotography) can be utilized in conjunction with this engineered cell-based assay for quantitative measurement of the bioluminescence response to microbial toxin activity at levels comparable to those permitted by commercial luminometers typically costing 30 times more than a CCD camera. The imaging device method of the present invention showed surprising sensitivity across various microbial toxins and cell lines. Thus, adopting the disclosed system and method is especially suitable for use where resources are limited and, further, the simplicity and reduced cost allow for expanded efficient microbial toxin testing with surprising sensitivity for the promotion of food safety in governmental and non-governmental agencies, including the military, public health departments, healthcare facilities, and the food industry.

A further advantage of the system of the invention over a luminometer is in the effective multiplexing of data measurements; the system quantifies the light emission of multiple assay samples simultaneously whereas the luminometer is a sequential analytic device. The light levels generated by, for example, the luciferase-catalyzed oxidation of luciferin to oxyluciferin were found to be proportional to microbial toxin concentration with a linear correlation $R^2=0.99$. Biologically active microbial toxin was assayed with a detection limit of 100 fg/mL. This detection limit, as discussed above, is a factor of $10^3$ improvement in sensitivity when compared to spleen cell proliferation bioassay, a factor of $10^4$ more sensitive compared to typical ELISA assays having a 1 ng/mL limit of detection, and a factor of $10^7$ advantage over the monkey and kitten live animal emetic assays where vomiting occurs in response to an administered dose of 10 mg of the toxin.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments and characteristics described herein and/or incorporated herein. In addition the invention encompasses any possible combination that also specifically excludes any one or some of the various embodiments and characteristics described herein and/or incorporated herein.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 30%, preferably by as much as 20%, and more preferably by as much as 10% to a reference quantity, level, value, or amount.

The term "consisting essentially of" excludes additional method (or process) steps or composition components that substantially interfere with the intended activity of the method (or process) or composition. This term may be substituted for inclusive terms such as "comprising" or "including" to more narrowly define any of the disclosed embodiments or combinations/sub-combinations thereof. Furthermore, the exclusive term "consisting" is also understood to be substitutable for these inclusive terms.

"Optional" or "optionally" means that the subsequently described event or circumstance may or may not occur, and that the description includes instances in which said event or circumstance occurs and instances where it does not. For example, the phrase "optionally comprising a defoaming agent" means that the composition may or may not contain a defoaming agent and that this description includes compositions that contain and do not contain a foaming agent.

By the term "effective amount" of a compound or property as provided herein is meant such amount as is capable of performing the function of the compound or property for which an effective amount is expressed. As is pointed out herein, the exact amount required will vary from process to process, depending on recognized variables such as the compounds employed and various internal and external conditions observed as would be interpreted by one of ordinary skill in the art. Thus, it is not possible to specify an exact "effective amount," though preferred ranges have been provided herein. An appropriate effective amount may be determined, however, by one of ordinary skill in the art using only routine experimentation.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims. Although any methods and materials similar or equivalent to those described herein can be used in the practice or testing of the present invention, the preferred methods and materials are herein described. Those skilled in the art may recognize other equivalents to the specific embodiments described herein which equivalents are intended to be encompassed by the claims attached hereto.

The claimed invention is:

1. A system for detecting a microbial toxin in a food matrix, the system comprising: (a) an imaging device operable to detect a luminescent signal; (b) a lens attached to the imaging device; (c) optionally at least one secondary lens; (d) an analysis plate having at least one well to hold a sample containing the microbial toxin; (e) a cell line having a reporter gene expressing a product capable of reacting directly or indirectly with the microbial toxin to produce the luminescent signal; (f) optionally an accessory cell line which when exposed to the microbial toxin displays the microbial toxin as an antigen on its surface to activate expression of the reporter gene expressing the product capable of reacting directly or indirectly with the microbial toxin to produce the luminescent signal; and (g) an image processing system operable to receive the luminescent signal detected by the imaging device and convert the luminescent signal to a quantitative measurement correlated to an amount of the microbial toxin present in the sample; wherein the imaging device and the lens are not part of a microscopic system; and wherein said system does not include the use of a microscope, and wherein the microbial toxin comprises an active microbial toxin, and wherein a lower limit of detection of the active microbial toxin is about 1 fg/mL.

2. The system of claim 1, wherein the microbial toxin is at least one subtype of staphylococcal enterotoxin.

3. The system of claim 1, wherein the microbial toxin is at least one staphylococcal enterotoxin subtype selected from the group consisting of: SEA, SEB, SEC, SED, SEE, and combinations thereof.

4. The system of claim 1, wherein the microbial toxin is an active microbial toxin and wherein the cell line having the reporter gene construct expressing the product capable of reacting directly or indirectly with the active microbial toxin to produce the luminescent signal does not react with, if any is present, an inactive microbial toxin.

5. The system of claim 1, wherein the microbial toxin is an isolated target microbial toxin.

6. The system of claim 1, wherein the food matrix is selected from the group consisting of: a solid food matrix, a semi-solid food matrix, and a liquid food matrix.

7. The system of claim 1, wherein the imaging device uses an image sensor comprising a charge-coupled device or a complimentary metal-oxide-semiconductor.

8. The system of claim 1, wherein the imaging device is a cooled astronomical camera.

9. The system of claim 1, wherein the secondary lens is selected from the group consisting of: close-up filter, close-up lens, macro filter, and combinations thereof.

10. The system of claim 1, wherein the analysis plate having the at least one well to hold the sample containing the microbial toxin comprises a light-absorbing material to absorb ambient light and/or reduce transfer of light between wells thereby increasing sensitivity of the luminescent signal detection from each individual well.

11. The system of claim 1, wherein the cell line having the reporter gene expressing the product capable of reacting directly or indirectly with the microbial toxin to produce the luminescent signal is a Jurkat T-cell line engineered with a luciferase reporter gene.

12. The system of claim 1, wherein the product capable of reacting directly or indirectly with the microbial toxin to produce the luminescent signal is selected from the group consisting of: green fluorescent protein, blue fluorescent protein, and luciferase.

13. The system of claim 1, wherein the product capable of reacting directly or indirectly with the microbial toxin to produce the luminescent signal is luciferase.

14. The system of claim 1, wherein the reporter gene is under control of nuclear factor of activated T-cell response element.

15. A method of detecting a microbial toxin using the system of claim 1, the method comprising: (a) isolating the microbial toxin from a food matrix to create an isolated microbial toxin for analysis with an imaging device operable to detect a luminescent signal and a lens attached to the imaging device; (b) placing the isolated microbial toxin in a sample well on an analysis plate; (c) optionally exposing the isolated microbial toxin to an accessory cell line which when exposed to the microbial toxin displays the microbial toxin as an antigen on its surface to activate expression of a reporter gene expressing a product capable of reacting directly or indirectly with the microbial toxin to produce a luminescent signal; (d) exposing the isolated microbial toxin or the accessory cell line to a cell line having the reporter gene expressing the product capable of reacting directly or indirectly with the microbial toxin to produce the luminescent signal; (e) detecting the luminescent signal with the imaging device; (f) processing the luminescent signal with an image processor to create a processed luminescent signal; and (g) converting the processed luminescent signal to a quantitative measurement correlated to an amount of the microbial toxin present in the food matrix; wherein the imaging device and the lens are not part of a microscopic system; and wherein said method does not include the use of a microscope.

16. The method of claim 15, wherein the isolated microbial toxin is in a form selected from the group consisting of: a solution; a suspension; a precipitate; and a crystalline.

17. An apparatus for detecting a microbial toxin in a food matrix, the apparatus comprising: (a) an imaging device operable to detect a luminescent signal; (b) a lens attached to the imaging device; (c) optionally at least one secondary lens; (d) an analysis plate having at least one well to hold a sample containing the microbial toxin; (e) a cell line having a reporter gene expressing a product capable of reacting directly or indirectly with the microbial toxin to produce the luminescent signal; (f) optionally an accessory cell line which when exposed to the microbial toxin displays the microbial toxin as an antigen on its surface to activate expression of the reporter gene expressing the product capable of reacting directly or indirectly with the microbial toxin to produce the luminescent signal; and (g) an image processing system operable to receive the luminescent signal from every well on the analysis plate detected by the imaging device and convert the luminescent signal to a quantitative measurement correlated to an amount of the microbial toxin present in the sample of each well; wherein the imaging device and the lens are not part of a microscopic system; and wherein said apparatus does not include the use of a microscope; and wherein a lower limit of detection of the microbial toxin is about 1 fg/mL.

18. A method of detecting a microbial toxin in a food matrix using the apparatus of claim 17, the method comprising: (a) preparing the food matrix for analysis with an imaging device operable to detect a luminescent signal and a lens attached to the imaging device; (b) placing the food matrix in a sample well on an analysis plate; (c) optionally exposing the food matrix to an accessory cell line which when exposed to the microbial toxin in the food matrix displays the microbial toxin as an antigen on its surface to activate expression of a reporter gene expressing a product capable of reacting directly or indirectly with the microbial toxin to produce a luminescent signal; (d) exposing the food matrix or the accessory cell line to a cell line having the reporter gene expressing the product capable of reacting directly or indirectly with the microbial toxin to produce the luminescent signal; (e) detecting the luminescent signal with the imaging device; (f) processing the luminescent signal with an image processor to create a processed luminescent signal; and (g) converting the processed luminescent signal to a quantitative measurement correlated to an amount of the microbial toxin present in the food matrix; wherein the imaging device and the lens are not part of a microscopic system; and wherein said method does not include the use of a microscope.

19. The method of claim 18, wherein the isolated microbial toxin is in a form selected from the group consisting of: a solution; a suspension; a precipitate; and a crystalline.

\* \* \* \* \*